United States Patent [19]

Beritashvili et al.

[11] Patent Number: 5,028,308

[45] Date of Patent: Jul. 2, 1991

[54] APPARATUS FOR THE ELECTROPHORETIC SEPARATION OF HIGH-MOLECULAR DNA IN GEL

[76] Inventors: David R. Beritashvili, ulitsa D. Ulyanova, 4, korpus, 1, kv. 33; Lev V. Karklit, ulitsa Bolotnikovskaya, 38, korpus 5, kv. 2; Konstantin G. Skryabin, ulitsa D. Ulyanova, 1/61, kv. 191; Evgeny N. Tverdokhlebov, ulitsa Dnepropetrovskaya, 31, kv. 207; Andrei I. Poletaev, ulitsa Profsojuznaya, 132, korpus 4, kv. 5, all of Moscow, U.S.S.R.

[21] Appl. No.: 328,072

[22] PCT Filed: May 26, 1988

[86] PCT No.: PCT/SU88/00124

§ 371 Date: Feb. 17, 1989

§ 102(e) Date: Feb. 17, 1989

[87] PCT Pub. No.: WO88/10423

PCT Pub. Date: Dec. 29, 1988

[30] Foreign Application Priority Data

Jun. 19, 1987 [SU] U.S.S.R. .................. 4286173

[51] Int. Cl.$^5$ ............ G01N 27/26; B01D 57/02
[52] U.S. Cl. .................. 204/299 R; 204/182.8
[58] Field of Search ............ 204/299 R, 182.8, 180.1

[56] References Cited

U.S. PATENT DOCUMENTS 4,473,452  9/1984  Cantor et al. .................. 204/182.8

FOREIGN PATENT DOCUMENTS 0256737  2/1988  European Pat. Off. ........ 204/299 R
8700635  1/1987  PCT Int'l Appl. ............ 204/299 R Primary Examiner—John F. Niebling
Assistant Examiner—John S. Starsiak, Jr.
Attorney, Agent, or Firm—Burgess, Ryan & Wayne

[57] ABSTRACT

An apparatus has an electrophoretic chamber in which groups of electrodes are positioned along sides of an equilateral quadrangle. Electrodes within each group are positioned in equally spaced relation to one another and are connected to a power supply via a switching circuit.

1 Claim, 2 Drawing Sheets

APPARATUS FOR THE ELECTROPHORETIC SEPARATION OF HIGH-MOLECULAR DNA IN GEL

TECHNICAL FIELD

The invention relates to the separation and analysis of biopolymers by the method of electrophoresis, and more specifically, it deals with apparatuses for electrophoretic separation of high-molecular DNA in gel.

BACKGROUND OF THE INVENTION

Separation of mixtures of biopolymers, in particular of DNA molecules of a size greater than $5 \cdot 10^4$ nucleic base pairs is based on the pulse electrophoresis involving the consecutive creation of crossing electric fields in gel in which a mixture of high-molecular DNA is introduced.

Known in the art is an apparatus for separating mixtures of DNA molecules Carle GP (Frank M. and Olson M. V. Electrophoretic Separation of Large DNA molecules by "Periodic Inversion of the Electric Field". Science. v. 232. 1986, pp. 65–68), in which a rectangular horizontally extending electrophoretic chamber has two opposed linear electrodes between which a block of gel is placed. Voltage from a power supply is applied through a switching circuit to the electrodes during $\frac{3}{4}$ of a preset time period in the direct polarity and during $\frac{1}{4}$ of the same time period in the inverted polarity, and this switching cycle is repeated for a large number of times. Movement of DNA molecules is thus regularly reversed at 180°. This angle is not an optimum angle for a large range of molecular mass values of DNA molecules being separated so that it is not possible to isolate individual fractions of DNA of a size greater than $2 \cdot 10^6$ base pairs. In addition, reciprocations of molecules within the gel block result in an increase in the time of separation of the initial mixture or in a lower productivity of the apparatus.

Known in the art is an apparatus (G. Chy, D. Vollarth, R. W. Davis. Separation of Large DNA Molecules by Contour-Clamped Homogeneous Electric Fields. Science. v. 234. 1986. pp. 1582–1585), in which six groups of point-like electrodes extending vertically with respect to the surface of a gel block define a hexahedron which is electrically short-connected through identical resistors, the gel block being placed inside the hexahedron. Voltage from a constant polarity power supply is applied consecutively through a switching circuit to respective pairs of opposed groups of electrodes. A third pair of groups of electrodes remains passive and designed for creating a homogeneous electric field between the electrodes. DNA molecules move with a change in direction of movement at 120° upon every switching of the voltage. With the same dimensions of the chamber as in the above described apparatus, the gel block should be of a smaller size, hence with a smaller number of samples thus lowering productivity of the apparatus. In addition, power output of the power supply should be doubled as current flowing through the electrodes should be at least equal to current flowing through buffer solution covering the gel block.

Known in the art is an apparatus for the separation of high-molecular weight DNA in a gel (U.S. Pat. No. 4,473,452) which makes it possible to separate mixtures of DNA molecules with molecular masses from $5 \cdot 10^4$ to $9 \cdot 10^6$ base pairs. A square-shaped electrophoretic chamber of the apparatus accommodates four groups of electrodes, groups of point-like electrodes being provided on two adjacent walls and electrically connected to each other within each group, and two individual point-like electrodes being provided on the other pair of adjacent walls of the chamber in the immediate vicinity to the ends of the two opposed groups of electrodes. Voltage of negative polarity is applied from a power supply source through a switching circuit during identical time intervals to one group of electrodes and voltage of positive polarity is applied, to the opposed point-like electrode. Subsequently voltage is applied in the same manner to the second group of electrodes and to the second individual electrode. Crossing curvilinear electric fields are thus created in the gel block placed in the electrophoretic chamber to cause DNA moleculaes to move along complex trajectories the direction of which changes within the range from 90° to 180° moving close to the point-like electrodes.

Curvilinear configuration of fields created in the prior art apparatus results, first, in a curvature of tracks of individual DNA fractions in the gel thus substantially hampering determination of their molecular mass and calls for the employment of special correcting programs for automatic processing of results, e.g. when gel scanners are used. Second, the number of concurrently separated DNA molecules is small as the end tracks are curved so that they may even come out of the gel into the buffer solution.

SUMMARY OF THE INVENTION

The invention is based on the problem of providing an apparatus for the electrophoretic separation of high-molecular weight DNA in a gel in which position of electrodes in an electrophoretic chamber makes it possible to define tracks of molecules extending in parallel with one another and linear configuration of fronts of separated individual fractions owing to the creation of homogeneous electric fields in the chamber ensuring identical separation conditions over the entire area of a gel block.

This problem is solved by that in an apparatus for the electrophoretic separation of high-molecular weight DNA in a gel, comprising an electrophoretic chamber accommodating four groups of electrodes connected to a power supply via a switching circuit, according to the invention, the four groups of electrodes are identical and are positioned along sides of an equilateral quadrangle surrounding a gel block, the electrodes within each group being positioned in equally spaced relation to one another.

The four groups of electrodes are preferably positioned along sides of a rhombus, the opposed pairs of electrode groups being movable, each group of electrodes comprising auxiliary electrodes positioned along lines which are extensions of the rhombus sides beyond vertices of the larger internal angles, the length of the lines being determined as $$1 = \frac{h}{tg\alpha},$$

wherein $\alpha$ is the smaller internal rhombus angle and h is the distance between the opposed sides of the rhomb.

The invention makes it possible to increase productivity of separation of mixtures of DNA molecules owing to utilization of the entire area of the gel block;

enhance accuracy of determination of molecular mass of individual separated DNA fractions owing to the use of a single marker; improve efficiency of separation of mixtures of DNA molecules within a broad range of molecular mass values owing to a change in the angle $\alpha$ during separation; make use of gel scanners for automatic processing of separation results.

BRIEF DESCRIPTION OF THE DRAWINGS

The invention will now be described in detail with reference to specific embodiments illustated in the accompanying drawings, in which.

BEST MODE FOR CARRYING OUT THE INVENTION

Figure 1:
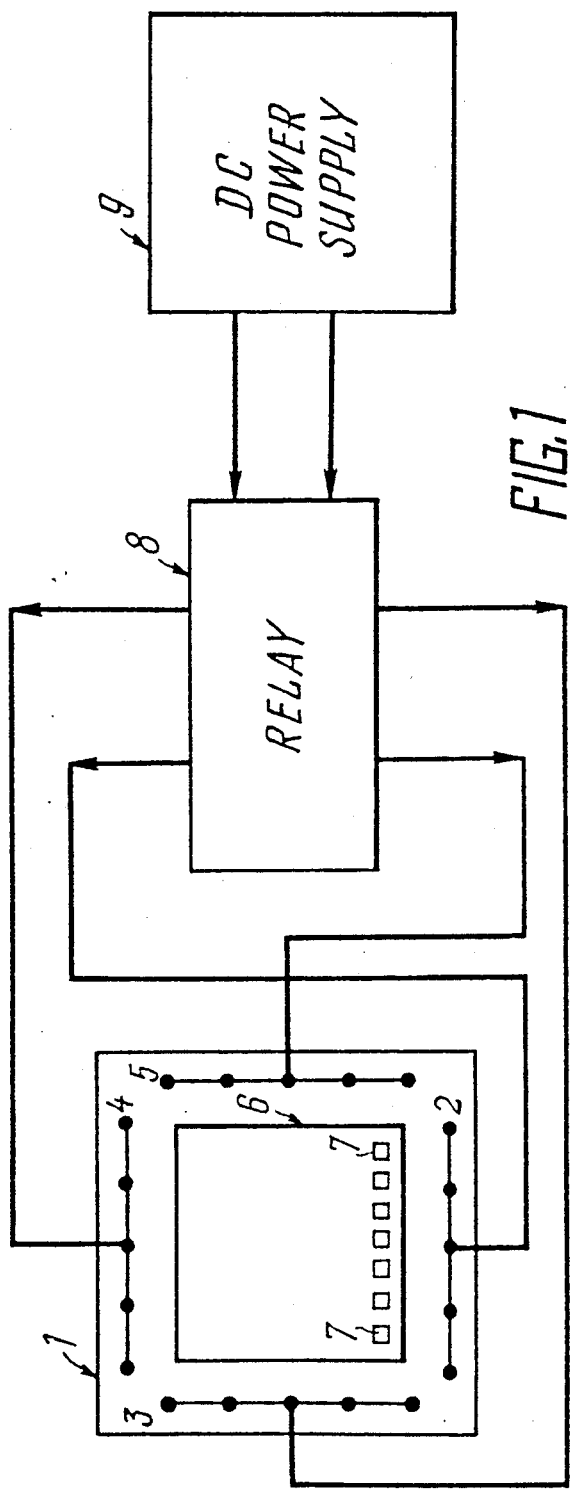
FIG. 1 is a block-diagram of a first embodiment of an apparatus for the electrophoretic separation of high-molecular weight DNA in a gel according to the invention.

An apparatus for the electrophoretic separation of high-molecular weight DNA in a gel comprises an electrophoretic chamber 1 (FIG. 1) of rectangular configuration with four identical groups 2,3,4 and 5 having identical numbers of equally spaced point-like electrodes electrically connected to one another through diodes (not shown in FIG. 1). The groups 2,3,4,5 of electrodes are mounted on a holder (not shown in FIG. 1) which serves as a top cover plate of the electrophoretic chamber 1 along sides of a square surrounding a block of gel 6 placed on the bottom of the chamber 1 and having samples 7 of mixtures of DNA molecules applied to one of its edges. The gel block 6 is covered by a layer of a buffer solution which allows current to flow between respective groups 2,3,4,5 of electrodes when voltage is applied thereto. The groups 2 and 4 of electrodes are electrically coupled to one output of a switching circuit 8, the groups 3 and 5 of electrodes are coupled to another output of the switching circuit 8 which has its input connected to an output of a power supply 9.

Figure 2:
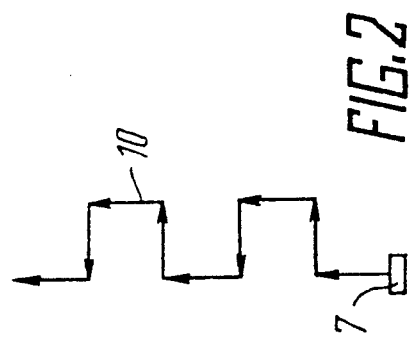
FIG. 2 shows a trajectory of movement of DNA molecules in gel obtained in the first embodiment of an apparatus according to the invention.

FIG. 2 shows a trajectory 10 along which each of molecules of the sample 7 of DNA moves when the groups 2,3,4,5 of electrodes are positioned along sides of a square.

Figure 3:
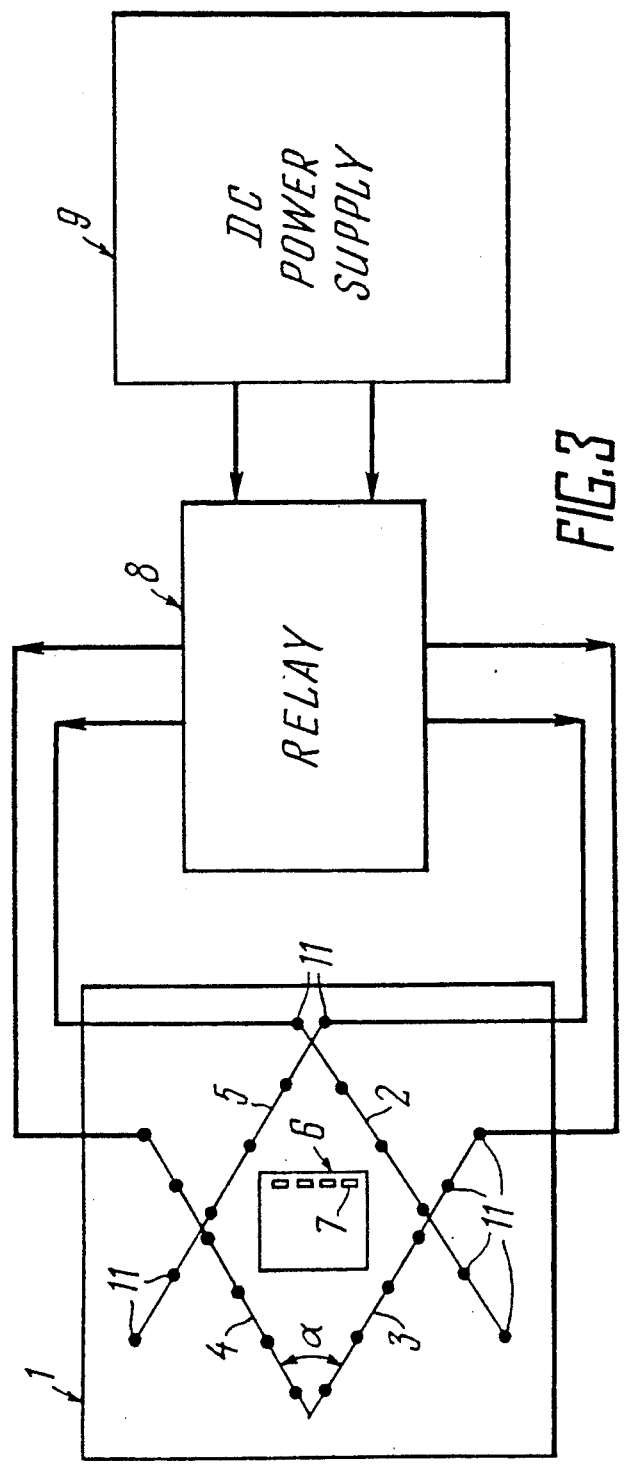
FIG. 3 is a block-diagram of a second embodiment of an apparatus for the electrophoretic separation of high-molecular weight DNA in a gel according to the invention.
Figure 4:
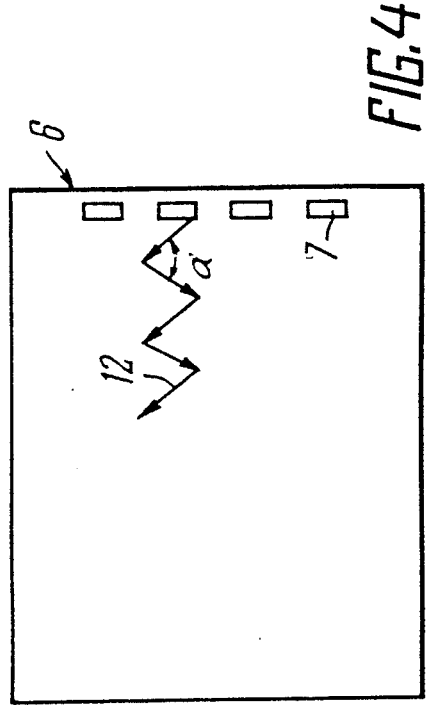
FIG. 4 shows a trajectory of movement of DNA molecules in gel obtained in the second embodiment of an apparatus according to the invention.

For obtaining a change in trajectories of DNA molecules in the sample 7 at an angle other than 90°, the groups 2,3,4,5 of electrodes (FIG. 3) are positioned along sides of a rhombus having its smaller internal angle chosen in advance, e.g. $\alpha = 60°$. Each group 2,3,4,5 comprises auxiliary electrodes 11 positioned along lines which are extensions of the sides of the rhombus beyond vertices of its larger internal angles and which are of a length $$l = \frac{h}{tg\alpha},$$

wherein h is the distance between the opposed sides of the rhombus. FIG. 4 shows a trajectory 12 of movement of molecules in the sample 7 of DNA in the gel block 6 with this position of the groups 2,3,4,5 of electrodes.

The apparatus for the electrophoretic separation of high-molecular weight DNA in a gel according to the invention functions in the following manner. The gel block 6 (FIG. 1) having samples 7 of mixtures of DNA molecules applied thereto is placed into the electrophoretic chamber 1 to extend in parallel with the walls thereof and is covered with buffer solution in contact with the electrodes of all the four groups 2,3,4,5 of electrodes. The power supply 9 is then energized, and positive voltage is applied to the group 4 of electrodes and negative voltage is applied to the group 2 of electrodes through the switching circuit 8. DNA molecules are arranged along lines of force of the electric field between the groups 2 and 4 of electrodes and start moving towards the group 4 which is at the positive potential. After a lapse of a preset time, the switching circuit 8 removes voltage from the groups 2,4 of electrodes, and positive voltage is applied to the group 3 of electrodes and negative voltage is applied to the group 5 of electrodes. DNA molecules 7 are rearranged along lines of force of the electric field which are not differently directed, the rearrangement time being different for molecules of different size, and start moving towards the group 3 of electrodes. After a lapse of the same time voltage is removed from the groups 3,5 of electrodes by the switching circuit 8 and is again supplied to the groups 2,4 with the same pattern of polarity as during the first voltage supply cycle. Then the switching circuit 8 removes voltage from the groups 2 and 4 after the same lapse of time and applies voltage to the groups 3 and 5 with a polarity which is reversed with respect to the polarity used during the second cycle of operation of the switching circuit 8. The above described cycles of switching of voltage from the power supply 9 are repeated until the lightest individual DNA fractions come to the end of the gel block 6 opposite to the site of application of the samples 7. The trajectory 10 of movement of DNA molecules with such an alternation of fields applied to the gel block 6 is shown in FIG. 2. It can be seen that upon each operation of the switching circuit 8 the molecules are turned at 90°. Owing to differences between rearrangement times for molecules of different size, i.e. owing to different molecular masses, the initial sample 7 of DNA is effectively separated when it contains molecules of a size ranging from $5 \cdot 10^4$ to $2 \cdot 10^6$ base pairs.

When the groups 2,3,4,5 of electrodes (FIG. 3) are positioned along sides of a rhombus, voltage is alternatively applied to the groups 2 and 4 (positive voltage to the group 4 and negative voltage to the group 2) and to the groups 3, and 5 (positive voltage to the group 3 and negative voltage to the groups 5). These voltage switching cycles are repeated until the separation process is completed.

For creating a homogeneous electric field at the point where the gel block 6 is positioned, all four groups 2,3,4,5 of electrodes have the auxiliary electrodes 11 positioned along lines which are extensions of the rhomb sides. This position of the groups 2,3,4,5 of electrodes ensures the trajectory 12 of movement of DNA molecules shown in FIG. 4.

In separating mixtures of DNA molecules containing both relatively small molecules of the order of $5 \cdot 10^4$ base pairs and relatively large molecules of the order of $5 \cdot 10^6$ base pairs, it is necessary to vary the angle $\alpha$ a fixed value of which is only optimum for a certain narrow range of molecular mass values.

Various embodiments of the apparatus ensuring the provision of a desired angle α and its variation during separation of DNA mixtures are possible. The most simple among them is that in which the groups 2,4 of electrodes (FIG. 1) are positioned on the bottom of the electrophoretic chamber 1 and the groups 3,5 of the electrodes are positioned on the top cover plate of holder which is mounted for a controlled rotation.

Therefore, positioning the four identical groups 2,3,4,5 of electrodes with equally spaced electrodes within these groups along sides of an equilateral quadrangle makes it possible to create at the point where the gel block 6 is placed homogeneous electric fields crossing at a preset angle, i.e. to ensure identical conditions for DNA molecule movement at every point over the surface of the gel block 6.

INDUSTRIAL APPLICABILITY

The invention may be successfully used in the biotechnology, molecular biology and genetics, biochemistry, biophysics as well as in the medicine and agriculture.

We claim:

1. An apparatus for the electrophoretic separation of high-molecular weight DNA in a gel, comprised of electrophoretic chamber (1) accommodating four groups (2,3,4,5) of electrodes connected, via a switching circuit (8), to a power supply (9), wherein said four groups (2,3,4,5) of electrodes are positioned along sides of a rhombus surronding a gel block (6), the opposed pairs of groups (2,4 and 3,5) of electrodes being movable, each group (2,3,4,5) of electrodes comprising auxiliary electrodes (11) positioned along lines which are extensions of the rhombus sides beyond the vertices of its larger internal angles the length of which being determined as $$l = \frac{h}{tg\alpha},$$

wherein h is the distance between the opposed sides of the rhombus and $tg\alpha$ is the tangent of the smaller internal angle of the rhombus, the electrodes within each of said groups (2,3,4,5) being positioned in equally spaced relation to one another.

* * * * *